US006197528B1

(12) United States Patent
Wu et al.

(10) Patent No.: US 6,197,528 B1
(45) Date of Patent: Mar. 6, 2001

(54) COMPOSITION OF IMMUNOTOXINS AND RETINOIDS AND USE THEREOF

(75) Inventors: YouNeng Wu, Bethesda; Richard J. Youle, Garrett Park, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/249,423

(22) Filed: Feb. 12, 1999

Related U.S. Application Data

(62) Division of application No. 08/238,997, filed on May 6, 1994, now Pat. No. 5,942,230.

(51) Int. Cl.[7] .................................................. G01N 33/567
(52) U.S. Cl. ............................................... 435/7.2; 436/63
(58) Field of Search ....................... 435/7.1, 7.2; 436/63, 436/64; 424/278.1

(56) References Cited

U.S. PATENT DOCUMENTS

| 4,894,227 | 1/1990 | Stevens et al. | 424/85.2 |
| 5,112,607 | 5/1992 | Hudson et al. | 424/85.91 |

OTHER PUBLICATIONS

Funatsu et al, "Conserved amino acid residues in ribosome–inactivating proteins for plants", *Biochimie* (1991) 73, pp. 1157–1161.

Montecucchi et al, "N–terminal sequence of some ribosome–inactivating proteins", *Peptide Protein Res.* 33, 1989, pp. 263–267.

Fong et al, "Minireview: Enzymatic Properties of Ribosome–Inactivating Proteins (RIPs) And Related Toxins", *Life Sciences*, (1991) vol. 49, pp. 1859–1869.

Gerald B. Dermer, "Another Anniversary for the War on Cancer", *Bio/Technology*, vol. 12, Mar. 1994, p. 320.

Rybak et al, "Monoclonal Antibodies Conjugated to Protein Toxins", *Clinical Use of Immunotoxins*, vol. 11, No. 2, May 1991.

Thorpe et al, Improved Antitumor Effects of Immunotoxins Prepared with Deglycosylated Ricin A–Chain and Hindered Disulfide Linkages, *Cancer Research*, 48, No. 22, pp. 6257–6623, Nov. 15, 1988.

Vitetta et al, "Redesigning Nature's Poisons to Create Anti–Tumor Reagents", *Science*, vol. 238, pp. 1015–1202, Nov. 1987.

Pastan et al, "Immunotoxins", *Cell*, vol. 47, pp. 641–648, Dec. 8, 1986.

Blakely et al, "Comparison of the Pharmacokinetics and Hepatotoxic Effects of Saporin and Ricin A–Chain Immunotoxins on Murine Liver Parenchymal Cells", *Cancer Research*, vol. 48, No. 24, pp. 6977–7338 (Dec. 15, 1988).

Laurent et al, "Effects of Therapy With T101 Ricin A–Chain Immunotoxin in Two Leukemia Patients", *Blood*, vol. 67, No. 6, pp. 1680–1687, Jun. 1986.

Grossbard et al, "Serotherapy of B–Cell Neoplasma With Anti–B4–Blocked Ricin: A Phase I Trial of Daily Bolus Infusion", *Blood*, vol. 79, No. 3 (Feb. 1992) pp. 576–585.

Wu et al, (Abstract) "Retinoic acid alters intracellular traffic and potentiates immunotoxins", *Proceedings of the American Association for Cancer Research*, vol. 35, Mar. 1994, pp. 503.

*Primary Examiner*—Sheela Huff
(74) *Attorney, Agent, or Firm*—Morgan & Finnegan, L.L.P.

(57) ABSTRACT

The present invention relates to compositions of retinoids plus immunotoxins. More particularly this invention relates to the use of retinoids to potentiate the activity of immunotoxins for treatment of mammalian diseases.

8 Claims, 11 Drawing Sheets

454A12-rRA (M)

454A12-rRA (M)

COMPOSITION OF IMMUNOTOXINS AND RETINOIDS AND USE THEREOF

This is a divisional of application Ser. No. 08/238,997 filed May 6, 1994 now U.S. Pat. No. 5,942,230.

FIELD OF THE INVENTION

The present invention relates generally to compositions and methods for the treatment or prevention of cancer, autoimmune diseases, viral, microbial, parasitic and fungal diseases in mammals. More specifically, this invention relates to the potentiation of immunoconjugates by retinoids.

BACKGROUND

Classic modalities for treatment of diseases such as human cancers, autoimmune diseases, viral, microbial, parasitic and fungal diseases include surgery, radiation, chemotherapy, antibiotics or combination therapies. However, extended therapy with these agents may cause greater morbidity than the underlying disease. Alternate therapies for preventing or treating human diseases are greatly needed. In the past decade immunotherapy has emerged as a new and promising method for treating cancers.

Immunotoxins are being used in the treatment of diseases such as cancers, autoimmune diseases, viral, microbial, parasitic and fungal diseases. In one approach, antibodies targeting tumor associated antigens or tumor specific antigens are administered as a form of treatment. To augment the therapeutic efficacy of the antibodies, the antibodies are often conjugated to cytotoxic drugs, toxins or radioisotopes. Monoclonal antibodies coupled to protein toxins, called immunotoxins, are being examined in numerous clinical trials for treatment of cancer and autoimmune diseases (Rybak, S. M., et al. (1991) *Immunology and Allergy Clinics of North America* 11:359–380). Subsequent to cell surface binding by the monoclonal antibody, the toxic protein subunit crosses the membrane surrounding the cytosol to reach the intracellular substrate. Ricin, for example, enzymatically inactivates ribosomes, inhibiting protein synthesis and causing cell death (Endo, Y., et al (1987) *J. Biol. Chem.* 262:5908–5912; Olsnes, S., et al. (1973) *Biochemistry.* 12:3121–3126; Olsnes, S., et al. (1976) *J. Biol. Chem.* 257:3985–3992). How the hydrophilic enzyme crosses into the cytosol is unknown, although endocytosis and intracellular routing to the proper compartment are required (Johnson, V. G., et al. (1991)"Intracellular Routing And Membrane Translation Of Diphtheria Toxin And Ricin" *In Intracellular Trafficking of Proteins.* 183–225 C. J. Steer and J. A. Hanover (eds) Karger (Basel)). The Golgi apparatus appears to be one compartment through which ricin must pass en route to the cytosol. Native ricin efficiently routes through the Golgi apparatus to the cytosol due to galactose binding sites on the ricin B chain (Gonatas, N., et al. (1975) *Exp. Cell Res.* 94:426–431; Hudson, T. H., et al. (1991) *J. Biol. Chem.* 266:18586–18592; Sandvig, K., et al. (1991) *J. Cell Biol.* 115:971–981; Youle, R. J., et al. (1987) *J. Biol. Chem.* 262:4676–4682). When the ricin B chain is removed and enzymatically active A chain is linked to monoclonal antibodies reactive with cell surface molecules such as the transferrin receptor, much less efficient entry into the cytosol ensues (Youle, R. J., et al. (1982) *J. Biol. Chem.* 257:1598–1601). Although the immunotoxin is rapidly endocytosed via the transferrin receptor, it does not traffic such that the enzymatically active A chain rapidly reaches the cytosol. In addition to ricin B chain, some drugs that cause alterations in the Golgi apparatus such the ionophore, monensin, and lysosomotropic amines cause a large increase in cell sensitivity to the immunotoxins (Casellas, P., et al. (1984) *J. Biol. Chem.* 259:9359–9364). Chloroquine (Laurent, G., et al. (1986) *Blood.* 67:1680–1687), a lysosomotropic agent, and the ricin B chain (Grossbard, M. L., et al. (1992) *Blood* 79:576–585) have been tested in man for their ability to improve the anti-cancer activity of immunotoxins.

Retinoids are a large family of molecules encompassing over three thousand members. Retinoic acid, a member of the retinoid family, is a morphogen that defines certain cell fates during development and has the potential to treat cancer by inducing tumor cell differentiation (Petkovich, M. (1992) *Ann. Rev. Nutr.* 12:443–471; Thaller, C., et al. (1991) *In Retinoids:* 10 Years On 89–108 J. H. Saurat (ed) Karger/Basel). Retinoid acid binds the retinoic acid receptor (RAR) causing it to form heterodimers with the retinoid X receptor (RXR) and induce gene transcription (Chambon, P., et al. (1991)"The family of retinoid acid nuclear receptors" In *Retinoids:* 10 Years On. 10–27 J. H. Saurat (ed), Karger/Basel; Kliewer, S. A., et al. (1992) *Nature.* 355:446–449; Zhang, X. K., et al. (1992) *Nature.* 355:441–446). In addition to the well accepted role of retinoids in transcription activation, some retinoids may have direct effects on cell second messengers (Evain-Brion, D., et al. (1991) "Retinoid Acid & Cellular Signal Transduction" In *Retinoids:* 10 Years On. 46–55; J. H. Saurat(ed) Karger/Basel).

Additional therapies that potentiate the toxicity of the immunotoxins to a high degree of specificity for the affected target cell would greatly facilitate treatment of human diseases with these immunotherapeutic agents.

SUMMARY OF THE INVENTION

This intention relates, in general, to compositions and methods of treating mammalian diseases. This invention provides a method of potentiating the efficacy of immunotoxins used in treating mammalian diseases by administration of retinoids with the immunotoxins.

It is an object of this invention to provide a in vitro method for assessing the ability of a retinoid to potentiate the activity of immunotoxins.

One aspect of the invention provides a method for inhibiting the growth of target cells using a composition of an immunotoxin and a retinoid.

It is yet another object of this invention to provide an in vivo method for assessing the ability of a retinoid to potentiate the activity of an immunotoxin.

It is a further object of the present invention to provide compositions comprising retinoids and immunotoxins for preventing or treating mammalian diseases.

It is another object of this invention to provide compositions comprising retinoids and immunotoxins for preventing or treating mammalian cancers.

It is yet another object of this invention to provide a method of potentiating the activity of immunoconjugates in the prophylactic or therapeutic treatment of mammalian diseases.

It is a further object of this invention to provide a kit comprising the compositions for use in the methods described herein.

DESCRIPTION OF THE FIGURES

FIG. 1A: U251 cells growing in 96-well plates were incubated with increasing concentrations of 454A12-rRA (circles) or rRA (squares) in the presence (●,■) and in the absence (○,□) of 10 μM retinoic acid in leucine-free RPMI1640 medium; FIG. 1B: K562 cells growing in 96-well plates were incubated with increasing concentrations of 454A12-rRA in the presence (●) or absence (○) of 10 μM retinoid acid; FIG. 1C: 9L cells were incubated with increasing concentrations of 454A12-rRA (circles) or tfn-rRA (squares) in the presence (●,■) or absence (○,□) of 10 μM retinoic acid. After 3 hours (hrs.) incubations $^{14}$C-leucine was added for another 1 hr. Cells were harvested and counted as described in Example 1.

In FIGS. 7C and 7D, cells were first stained with 5 μM $C_6$-NBD-ceramide, washed twice, and further incubated at 37° C. in the presence (FIG. 7D) or absence (FIG. 7C) of 10 μM all-trans retinoic acid for 2 hrs. without $C_6$-NBD-ceramide. Cells thus treated were mounted and photographed as described above.

FIG. 8A, control cell (X 10,000),; FIG. 8B, retinoic acid treated cells (X 10,000); FIG. 8C, control cells (X 20,000); FIG. 8D, retinoic acid treated cells (X 20,000).

(FIG. 9C) before fixing. Cells were then processed for electron microscopy (G, Golgi apparatus; M, mitochondrium; N, nucleus; thick arrow, vacuolized structures; X12,000).

DETAILED DESCRIPTION OF THE INVENTION

Figure 1A:
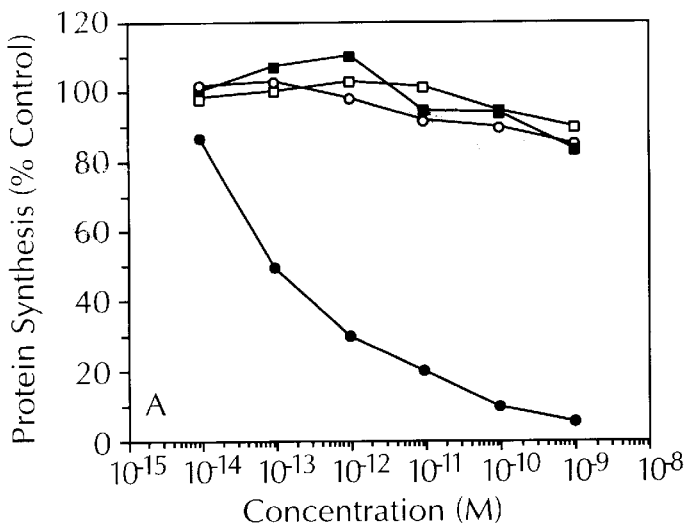
FIGS. 1A–1C shows the potentiation of 454A12-ricin A chain (rRA), transferrin (Tfn)-rRA, and rRA cytotoxicity by all-trans retinoic acid in U251, K562, and 9L cells.

For the purpose of a more complete understanding of the invention, the following definitions are described herein. Mammal includes, but is not limited to, humans, monkeys, dogs, cats, mice, rats, hamsters, cows, pigs, horses, sheep and goats.

Tissue includes, but is not limited to, single cells, whole organs and portions thereof. Biological samples includes, but is not limited to, tissues, primary cell lines of mammalian tissues, biopsy specimens, pathology specimens and necropsy specimens.

Cancer includes, but is not limited to malignant tumors, adenocarcinomas, carcinomas, sarcomas, malignant neoplasms, leukemias, breast cancer, ovarian cancer, rectal cancers, colon cancers, melanomas, lung cancer, or brain cancers. Examples of brain cancers or malignant brain neoplasms include, but are not limited by gliomas, glioblastoma, astrocytoma, oligodendroglioma, meningioma, medulloblastoma, ependymoma, and brain metastases from other organs. Such cancers may be caused by, chromosomal abnormalities, degenerative growth and developmental disorders, mitogenic agents, ultraviolet radiation (UV), viral infections, oncogenous, inappropriate tissue expression of gene, alteration in expression of a gene and presentation on a cell or carcinogenic agents.

Toxins or cytotoxins which may be used in the present invention include, but are not limited to, ricin A, abrin A chain, saporin, gelonin, plant ribosome inactivating proteins, trichosanthin, ribonucleases, modeccin and the like [Pastan, I. et al *Cell* 47 pp 641–648, 1986]. Angiogenin is a human blood vessel inducing protein which is also ribosome inactivating [St. Clair, D. K. et al, *Proc. Nat'l Acad. Sci.* 84, pp 8330–8334, 1987]. The toxin component of the immunotoxin in the composition of the present invention is composed of ricin, abrin, saporin, modeccin, tricosanthin, gelonin, angiogenin or the toxic portions of each toxin. The toxic portion includes the A chain or that portion of the A chain that confers toxicity against the targeted cell. Included in the ambit of the invention are peptides or portions thereof having amino acid sequences substantially homologous to the portion of the ricin A chain that confers toxicity against the targeted cell.

When the ricin A chain is used as the toxin for in vivo treatment it may be desirable to use the deglylosylated form. The form may be prepared from the natural sources or by recombinant means. Recombinant Ricin A chain lacking carbohydrate moieties has been expressed in *Escherichia coli* [O'Hare, M. et al. *FEBS Lett.* 216, 73, 1987; Gregg, E. O. et al. *J. Immunol.* 138, 4502, 1987]. Deglycosylation prevents an immunotoxin from binding to liver cells and, in vivo, results in more effective delivery to the target cell with significantly less hepatotoxicity [Vitetta et al *Science* 238, p 1098, 1987; Blakey et al *Cancer Research*, Vol. 48 (22) pp 6396–6403, 1988; Pastan, I. et al *Cell* 47, p 641, 1986].

One skilled in the art will appreciate that retinoids are a very large family of molecules. Examples of retinoids that can be used in the compositions and methods include any retinoids which when used in combination with an immunotoxin potentiates the activity of the immunotoxin against a target cell in vitro, ex vivo, or in vivo, or that potentiates the activity of the immunotoxin in the prevention or treatment of diseases. These retinoids include but are not limited tr, retinoic acids such as, all-trans retinoic acids, 13-cis retinoic acid, retinols, such as all-trans retinol, 13 cis retinol or 9-cis retinol. Derivatives or analogs of the retinoids that function to potentiate the activity of immunotoxin on target cells in vitro, ex vivo, or in vivo, as well as those derivatives and analogs of retinoids that potentiate the activity of immunotoxin in the prevention or treatment of diseases are also encompassed by this invention.

Current approaches to cancer, chemotherapy and other immunological therapies for other diseases focus on the use of cell-specific antibodies bonded to immunotoxins in order to inhibit the growth or kill a specific target population of mammalian cells. Ideally, immunotoxin should discriminate to a high degree between target and non-target cells. The critical point is the development of immunotoxins that are highly toxic for a specific target population of cells. Immunotoxins composed of toxins and cell-reactive antibodies directed against determinants on microorganisms, neoplastic cells and virally infected cells have been used to form cell-specific immunotoxins (Vitetta, E. S. *Science* 233, pp 1098–1104, 1987; Pastan, I. et al *Cell* 47, pp 641–648, 1986). Various immunotoxins are disclosed in Pastan et al, U.S. Pat. No. 4,545,985; Pastan et al. U.S. Pat. No. 4,892, 827, Biogen WO90/04414 published May 3, 1990.

The composition of the present invention comprises an immunotoxin, or more than one immunotoxin, in combination with at least one or more retinoids. The components of immunotoxin plus retinoids provide a composition that is more effective in inhibiting the growth or more effective in killing the appropriate target cell while having no or minimal effect on non-targeted cells as compared to either component separately. The advantage of the combination of immunotoxin plus retinoid is that the amount of immunotoxin necessary to achieve growth inhibition or killing of a target cell or the amount of immunotoxin necessary to achieve a therapeutic effect in vivo is lower than the amount of immunotoxin necessary to achieve an effect when immunotoxin, alone, is used. The advantage of the composition in vivo is a reduction of the nonspecific toxicity to vital organs such as the liver, spleen or kidney that is often observed in therapies using immunotoxin alone.

The toxin portion of the immunotoxin may be conjugated to a variety of antibodies or antibody fragments that recognize specific cell surface receptors or antigen on the target cell, such receptors or antigens are not found or are found in few numbers on non-targeted cells. The antibody or antibody fragment confers the selective binding of the immunotoxins to the targeted cell, for example a tumor associated antigen or tumor specific antigen on targeted tumor cells. A wide range of antibodies recognizing cell surface antigens are known in the art and are also commercially available (Waldmann, T. A. *Science* 1991, 252:1657–1662). Selection among these antibodies or antibody fragments for constructing an immunotoxin is on the basis of specificity for the target cells to be treated. Some antibodies of particular interest for targeting cells is anti-epidermal growth factor receptor antibodies, anti-interleukin 2 antibodies, anti-transferrin receptor antibodies, anti-CD5 antibodies, anti-CD4 antibodies and the like. Such antibodies may be monoclonal, polyclonal, single-chain or antiidiotype antibodies. Such antibodies may be chimeric antibodies or humanized antibodies constructed by conventional methods so as to be less immunogenic to the mammal. These antibodies can be generated by standard methods known in the art. The toxin may be coupled to the antibody by covalent bonds or chemical bonds and purified by conventional methods known in the art. The following references provide examples of methods of conjugating an antibody or ligand to a toxin: Pastan et al U.S. Pat. No. 4,545,985; Pastan, I. et al *Cell* 47:641–648, 1986; Vitetta, E. S. et al *Science* 238, 1098–1104, 1987; Thorpe, P. E. *Cancer Res.* 48:6396–6403, 1988; and Blakey, D. C. et al *Cancer Res.* 48:6977–7338, 1988. Immunotoxins may also be genetically produced by methods known to one skilled in the art (Pastan, I. et al *Science* 1994, 254:1173–1177; Nicholls, P. J. et al *J. Biol. Chem.* (1993) 268(7):5302–5308).

Alternative to antibodies, the toxin portion of the immunotoxin may be conjugated to a variety of ligands such as peptides, proteins and growth factors that react with specific receptors on the target cells. Some of these include but are not limited to epidermal growth factor, colony stimulating factor, sarcoma growth factors, melanocyte stimulating hormone (MSH), somatostatin, glycogen, insulin, transferrin, low density lipoprotein, calcitonin, $\alpha_2$-macroglobulin, viral envelop glycoproteins, Interleukins, interferons, lysine bradykinin and the like.

The present invention relates to the use of retinoids to potentiate the activity of immunotoxin in the prophylactic and therapeutic treatment of diseases in mammals. One in vivo application of the composition of the present invention is for the treatment of cancer caused by malignant cells of various types. Another use of the composition of the present invention is in bone marrow transplantation for the destruction of activated T lymphocytes that contribute to the development of graft-versus-host disease. After removed from a donor, bone marrow is treated in vitro with an immunotoxin such as anti-Thy 1.2-ricin A chain plus retinoid. The treated cells, devoid of activated T lymphocytes, is injected into a recipient.

Another use of the composition of the present invention is in autologous bone marrow transplantation. In the treatment of certain leukemias and lymphomas, bone marrow is harvested from a patient, treated with the composition of immunotoxin plus a retinoid to kill contaminating cancer cells and placed in storage. Subsequently, the patient is given extremely large doses of drugs and radiation to kill all remaining cancer cells. To rescue the patient, the purged bone marrow, now free of cancer cells, is reinfused.

Another use for the composition of the present invention includes destruction of activated T cells in vivo in order to allow organ graft survival or to arrest or prevent diseases such as diabetes, which may be caused by such cells.

Autoimmune diseases where anti-"self" antibodies are responsible for disease, may be treated with a composition of the present invention in which the immunotoxin is directed against the idiotype of the offending antibody-producing B cells. Examples of autoimmune conditions that may benefit by treatment using the composition of the present invention include, but are not limited to, graft-versus-host disease, organ transplant rejection, type I diabetes, multiple sclerosis, rheumatoid arthritis, systemic lupus erythematosus, myasthemia gravis and the like.

The composition of the present invention is also useful in treating diseases caused by infectious agents that infect a target cell population. Such agents including but are not limited to viruses, such as HIV, measles virus, bacteria, yeast, fungi, parasites such as plasmodium and the like.

The present invention includes a method of treating target cells in vitro or ex vivo in a mixture of target and nontarget cells. The method entails culturing the mixture of cells with retinoid and immunotoxin in an amount effective to inhibit the growth or to kill the target cells, and having no or minimal effect on non-target cells. The retinoid and immunotoxin may be added individually or together as a composition to the mixture. The effect of the treatment on the target cells may be determined by various methods known in the art including morphological examination, immunoassays, vital staining and the like. The treated cells devoid or significantly reduced in target cells may be kept in culture or injected into a mammal. The method is useful in removing selected target cells from a mixture of target and non-target cells. The target cells include, but are not limited to malignant cells, virally-infected cells, bacterially-infected cells, specific populations of T lymphocytes or B lymphocytes and the like.

Another aspect of the present invention relates to an in vitro assay to screen for retinoids that potentiate the activity of an immunotoxin. The screening method comprising the steps of (a) exposing mammalian target cells to a suitable immunotoxin and a retinoid to be screened for potentiating activity; and (b) assessing the potentiating activity of the retinoid for the immunotoxin against the target cells.

Examples of mammalian target cells that may be used in the screening method include but are not limited to cancer cells, primary cultures of mammalian cancer cells obtained from biological samples or continuous cell lines of mammalian cancer cells, such as U251 (a human glioma cell line, ATCC, 12301 Parklawn Dr., Rockville, Md. 20852), MCF-7 (a human breast cancer cell line; available through ATCC), K562 cells (a human erythroleukemia cell line, available through ATCC) a $L_2$ C Cells, (Gregg, E. N. et al *J. Immunol.* 1987, 138:4502–4508), 9L cells (available through ATCC), HIV-infected cells, *Mycobacterium tuberculosis*-infected cells, Measles virus-infected cells, Hepatitis-infected liver cells, *Legionella pneumophilia*-infected lung cells, and the like. A suitable immunotoxin for use in the screening assay is an immunotoxin capable of recognizing a cell surface antigen or receptor on the target cell and when internalized is capable of inhibiting the growth or killing the target cell. For example, an immunotoxin capable of recognizing tumor antigen on the target mammalian cancer cells and capable of inhibiting the growth or killing the target cancer cell may be used in the assay.

Examples of immunotoxins that may be used include, but are not limited to, the 454A12 monoclonal antibody coupled to ricin A (Frankel, A. et al *J. Biol. Response Modif.* 1985, 4:273–286), the 260F9 monoclonal antibody (Gregg, E. N. et al *J. Immunol.* 1987, 138:4502–4508) coupled to ricin A, or the M6 antibody (Gregg, E. N. et al *J. Immunol.* 1987, 138:4502–4508) coupled to ricin A. Additionally, the antibodies may be coupled to abrin A chain, saporin, gelonin, plant ribosome inactivating proteins, tricosunthin, modeccin, ribonucleases, angiogenin and the like or the toxic portion thereof.

The ability of the retinoid to potentiate the activity of the immunotoxin can be assessed by alteration in protein synthesis of the target cells exposed to the immunotoxin and retinoids, relative to control cells. By alteration is meant a decrease, diminution or abolishment of protein synthesis. Protein synthesis can be assessed by metabolic labeling of the cells or other methods known in the art. Potentiation by the retinoid may also be demonstrated by an enhanced inhibitory activity of the immunotoxin against targeted cells, as opposed to non-target cells, or a more rapid inhibitory effect of the immunotoxin against the targeted cells. Such enhanced or potentiated activity may be assessed by increased growth inhibition or increased toxicity or cell death of the target cells by the immunotoxin. Examples of retinoids to be used include, but are not limited to all trans retinoic acid, 13-cis retinoic acid, and all trans retinol.

The in vitro screening assay may be modified by persons skilled in the art to screen for retinoids, to screen for tumor cells that are capable of being effected by immunotoxin plus retinoid, and to screen for antibodies, ligands, toxins and combinations of each to use with a retinoid for treatment of target cells.

In another embodiment an in vivo assay is provided to assess the potentiating ability of retinoids on immunotoxin used in treating mammals afflicted with a disease, such diseases include but are not limited to cancer, autoimmune diseases, infectious diseases and the like. This in vivo assay comprises the steps of (a) providing an animal useful as a model for said disease of interest; (b) exposing said animal to a retinoid and an immunotoxin; and (c) evaluating the effect of the retinol and immunotoxin on the disease. Such an effect may be any measurable effect on the disease such as alleviation of the disease or a reduction in clinical manifestations of the disease in said animal exposed to said composition. Such clinical parameters to measure are known in the art and vary depending on the disease. The effect of the retinoid and immunotoxin is determined in relationship to control groups of animals, such animals include those treated with retinoid alone, those treated with immunotoxin alone, and nontreated animals and other appropriate controls known in the art.

The in vivo assay may be varied to screen for therapeutically useful retinoids in combination with a standard immunotoxin or to determine a therapeutically effective amount of an immunotoxin. The assay is also useful in screening therapeutically useful immunotoxins using a standard retinoid. The assay is also useful in screening for therapeutically useful antibodies, ligands and toxins for use with a retinoid and for titering the effective amount of each for use in vivo. An effective amount of the composition of immunotoxin plus retinoid is that amount that results in the alleviation of the disease being treated or a reduction in the clinical manifestations of the disease in the animal being treated.

Examples of animal models that may be used in screening therapeutically useful combinations of retinoids and immunotoxins include but is not limited to nude mice with human tumors, guinea pigs with $L_2C$ leukemia, rats with 9L glioma, HIV-animal models, animal models for infectious diseases, transgenic animal models for a disease of interest and the like. Examples of retinoids includes, but are not limited to all-trans retinoic acid, 13-cis retinoic acid, and all-trans retinol. Examples of immunoconjugates for use in the animal model include, but are not limited to 454A23-rRa, 260F9-rRa, M6-rRA and 5E9-ribonuclease.

The present invention includes methods of preventing or treating mammals with diseases. The diseases that are treatable by the composition of the present invention are diseases characterized as affecting a select target population of cells in a mammal afflicted by the disease. The present invention encompasses methods of treatment for cancer, autoimmune diseases, viral-,bacterial-, parasitic-, yeast-, fungal diseases and the like.

The composition of the present invention is effective in a method of treating HIV-infected cells both in vivo and ex vivo. For the ex vivo method, the HIV-infected cells are removed from the infected mammal and treated with an effective amount of retinoid and immunotoxin added individually or as a composition in vitro. The treated cells, devoid of the HIV-infected cells, are injected back into the mammal. A CD4-ricin A chain useful as the immunotoxin component is disclosed in Berger et al. U.S. Pat. No. 5,206,353.

In one embodiment of an animal model, nude mice are injected with cancer cells subcutaneously, intraperitoneally, I.V. or by any appropriate route. Examples of cancer cells that may be used, include but are not limited to, U251, K562, MCF7, and 9L. The animals are treated with transferrin-ricin A chain immunotoxin along. with all-trans retinoic acid. The animals are treated simultaneously with the composition comprising each component, i.e. immunotoxin plus the retinoid, or sequentially with each component of the composition. The all-trans retinoic acid may be administered regionally, intravenously or orally. The immunotoxin may be administered regionally or intravenously. The combination of immunotoxin and retinoid provides an effective amount, that amount being an amount of retinoid that potentiates the activity of the immunotoxin. By potentiation is meant a more rapid inhibition of killing of target cells involved in a disease condition by the immunotoxin as a result of the retinoid, or a lower effective concentration of immunotoxin as compared to the concentration of immunotoxin required to demonstrate an effect in the absence of retinoid. Potentiation may also be the amount of retinoid that results in the immunotoxin having an effect on a disease condition as compared to no effect on the disease condition by the immunotoxin in the absence of retinoid. The concentration of immunotoxin is approximately about 1 $\mu$g to approximately about 10 $\mu$g per nude mouse, use in conjunction with a retinoid. The concentration of the retinoic acid is approximately about 10 $\mu$M to approximately about 100 $\mu$M, used in combination with an immunotoxin. The present invention is not limited to a particular concentration of retinoid or immunotoxin for use in the animal model. A person skilled in the art can vary the concentrations to achieve optimization for different animal models using the methods disclosed in the present invention. The efficacy of the treatment in the animal model is assessed by measuring clinical changes in the disease such as measuring reduction in tumor size or animal survival after a period of time.

Of particular interest is a method for the treatment of brain tumors in a mammal, particularly a human, using the combination of each component separately or as a composition. A mammal afflicted with a brain tumor is treated with an effective amount of an immunotoxin and a retinoid. For example, in one embodiment transferrin-ricin A chain is used as the immunotoxin and all-trans retinoic acid is used as the retinoid. The immunotoxin is directly infused into the brain as disclosed in Bobo, R. H. et al. *Proc. Natl. Acad. Sci. USA* 1994, 91:2076–2080. The retinoic acid may be given orally or may be given in the form of a composition with the immunotoxin and infused directly into the brain. As a starting concentration of retinoids to use for direct infusion into the brain a concentration of approximately about 0.5 mM to approximately about 10 mM, or about 10 mM to about 100 mM may be used. In one embodiment 1 mM of retinoic acid is used. In the case of oral administration of the retinoic acid, a dose of about 500 to about 4000 mg/kg, or about 1000 to about 3000 mg/kg are administered. In a preferred embodiment, about 2000 mg/kg of retinoic acid is administered orally.

In another embodiment for treatment of brain tumors, the immunotoxin is monoclonal antibody 260F9-ricin A chain and the retinoid is trans retinoic acid. The immunotoxin is administered intravenously at a dose of about 0.1 to about 1 mg/kg, or about 0.2 to about 0.6 mg/kg. In a preferred embodiment, the immunotoxin is provided at a dose of about 0.4 mg/kg. The retinoid is trans retinoic acid which is administered orally at a dose of about 500 to about 4000 mg/kg, or about 1000 to about 3000 mg/kg. In a preferred embodiment, trans retinoic acid is administered at a dose of about 2000 mg/kg body weight. Both immunotoxin and trans retinoic acid are administered daily for 5 days. However, the method of treatment is in no way limited to a particular concentration of retinoid and may be varied for each mammal being treated and for each immunotoxin used. The composition is administered at regular intervals until a clinical change in disease can be detected. Such clinical parameters that may be assessed are a decrease in tumor size, a change in an MRI brain scan, and survival of the mammal. For instance, administration every month for a period of 6 months may result in reduction of the tumor size.

In yet another embodiment of this invention mammals at risk of reoccurrence of a cancer may be treated with the composition of the present invention.

The compositions directed against a mammalian cancers can be evaluated first in animal models, initially rodents, and in nonhuman primates and finally in humans.

The safety of the compositions and methods of treatment is determined by looking for the effect of treatment on the general health of the treated animal (weight change, fever, appetite behavior etc.) monitoring of generalized toxicity, electrolyte renal and hepatic function, hematological parameters and pharmacokinetic measurements. Pathological changes may be detected on autopsies. After initial testing in animals, cancer patients can be tested. Conventional methods are used to evaluate the response of the patient to determine the efficacy of the compositions.

Various immunotoxins have gone through clinical trials in humans for treatment of allogeneic and autologous bone marrow transplantation, blood-borne malignancies and solid tumors. (Ryback, S. M. et al *Immunol. and Allergy Clinics of North America*, 11:359–380, 1991). The dosing regimes and schedules used in these trials for testing of immunotoxins may be used as a general guideline for doses of immunotoxin to use in combination with a retinoid. For examples, Ryback et al 1991 disclose the use of anti-CD5-RTA ricin A-chain for treatment of graft-versus-host disease. A dose of 0.05 mg/Kg was administered I.V. to a patient daily for 14 days. The patient showed a complete response. It is anticipated that a dose lower than 0.05 mg/Kg of immunotoxin is effective when used in combination with a retinoid such as all-trans retinoic acid.

The retinoid and the immunotoxin may be supplied in kit form for use in the methods described herein. The kit may contain each component separately or each component combined to form a composition. Other components may be added to the kit, for example, chemotherapeutic drugs or immunosuppressive drugs and the like.

While it is possible for the composition comprising the immunoconjugate and retinoid to be administered in a pure or substantially pure form or to administer each component in pure or substantially pure form, it is preferable to present it as a pharmaceutical composition, formulation or preparation.

The formulations of the present invention, both for veterinary and for human use, comprise each component individually or as a composition as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of each component or the composition. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating each component separately or as a composition of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the MART-1 protein, peptides and analogs thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the compositions or of each individual component of the present invention may be for either a prophylactic or therapeutic purpose. When provided prophylactically, the composition is provided in advance of any evidence or in advance of any symptom of disease. The prophylactic administration of the composition serves to prevent or attenuate a disease in a mammal. When provided therapeutically, the composition is provided at (or shortly after) the onset of the disease or at the onset of any symptom of the disease.

All books, articles, or patents referenced herein are incorporated by reference. The following examples illustrate to various aspects of the invention but are in no way intended to limit the scope thereof.

EXAMPLE 1

In Vitro Potentiating Activity of Retinoids

Materials

All-trans retinoic acid was purchased from Sigma Chemical Co. (St. Louis, Mo.) and Calbiochem (San Diego, Calif.); brefeldin A, 13-cis retinoic acid, all-trans retinol, 13-cis retinol, all-trans retinal, 9-cis retinal and 13-cis retinal all from Sigma; C6-NBD-ceramide and fluorescein labeled goat anti-mouse IgG conjugate from Molecular Probes; 53FC3 MAb against mannosidase II was a generous gift from Dr. Lippincott-Schwartz (NIH) as described in Lippincott-Schwartz, J. et al *J. Cell Biol.* 1991, 112:567–577, Lippincott-Schwartz, J. et al. *Cell* 1989, 56:801–813; Lippincott-Schwartz et al *Cell* 1991, 67:601–616.; 1,25-dihydroxy vitamin $D_3$ and L-3,3',5-triiodothyronine(T3) were from Calbiochem; 454A12-rRA was prepared as described (Frankel, A., et al. (1985) *J. Biol. Response Modif.* 4:273–286); diphtheria toxin and Pseudomonas exotoxin were obtained from List Biological Co.; transferrin-CRM107 was prepared as described by Johnson et al (Johnson, V. G., et al. (1988) *J. Biol. Chem.* 263:1295–1300) and transferrin-PE was a generous gift from Dr. Aslak Godal (Hafslund Nycomed); 260F9-rRA (Frankel, A., et al. (1985) *J. Biol. Response Modif.* 4:273–286) and M6-rRA (Gregg, E. N., et al. (1987) *J. Immunol.* 138:4502–4508) were prepared as described; and transferrin-rRA was a generous gift from Dr. Jerry Fulton, available from Inland Laboratories, Inc.

Cell Lines

U251 (human glioma) cells and MCF-7 (human breast cancer) cells, and 9L (rat glioma) were grown in Dulbecco's modified Eagle's medium containing 10% fetal calf serum, 2 mM glutamine, 1 mM sodium pyruvate, 0.1 mM nonessential amino acids, and 10 µg/ml gentamycin. K562 (human erythroleukemia) cells were grown in RPMI 1640 containing 10% fetal calf serum, 2 mM glutamine, 1 mM sodium pyruvate, 0.1 mM non-essential amino acids, and 10 µg/ml gentamycin; $L_2C$ cells, a spontaneous transplantable B cell leukemia, were maintained by serial passage in inbred strain 2 guinea pigs as reported previously (Gregg, E. N., et al. (1987) *J. Immunol.* 138:4502–4508). $L_2C$ Cells were harvested from the peripheral blood and purified in Lymphocyte Separation Medium (Organon Teknika, Durham, N.C.), washed three times with Hanks balanced saline solution (HBSS) and resuspended in leucine-free RPMI 1640 for cytotoxicity assay.

Protein Synthesis Assay

Protein synthesis inhibition by DT, PE, ricin, and immunotoxins was determined as described previously (Wu, Y. N., et al. (1993) *J. Biol. Chem.* 268:10686–10693). Briefly, cells were plated at concentrations of $2 \times 10^5$ cells/ml in 96-well microtiter plates overnight in DMEM complete medium. Retinoic acid (15 mM in dimethyl sulfoxide, DMSO) and brefeldin A (BFA, 10 mg/ml in ethanol) stock solutions were diluted into leucine-free RPMI 1640 medium to the appropriate concentrations. The same amount of DMS0 and/or ethanol were added in the control solutions. After removing the complete DMEM medium, cells were incubated in the above leucine-free RPMI 1640 medium containing increasing concentrations of protein toxins with or without retinoic acid or other retinoids and/or BFA for 3 hrs followed by a 1 hr pulse with 0.1 µCi $^{14}$C-leucine. Cells were harvested onto glass fiber filters using a PHD, cell harvester, (Cambridge Technology, Inc., Cambridge, Mass.), washed with water, dried with ethanol, and counted. The results were expressed as the percentage of $^{14}$C-leucine incorporation in mock-treated control cells.

Vital Staining of the Golgi Apparatus $C_6$-NBD-ceramide was used to stain the Golgi apparatus in living cells (Lipsky, N. G., et al. (1985) *Science*. 228:745–747). Cells were treated with retinoic acid either before $C_6$-NBD-ceramide staining or after staining. In the case of $C_6$-NBD-ceramide staining after retinoic acid exposure, cells plated on cover slips were incubated in leucine-free RPMI1640 containing 10 µM retinoic acid or media containing an equivalent amount of DMSO in control cells. After two hrs, the above medium was removed and fresh medium containing 5 µM $C_6$-NBD-ceramide was added and incubated at 2° C. for 1 hr followed by a further incubation at 37° C. for 30 min. After staining, coverslips with labeled cells were mounted for fluorescence microscopy. In the case of $C_6$-NBD-ceramide staining before retinoic acid exposure, cells were first incubated with 5 µM $C_6$-NBD-ceramide at 2° C. for 60 min, the medium was removed and washed twice followed by a further incubation at 37° C. for 2 hrs in the presence or absence of 10 µM retinoic acid. Cells thus treated were mounted for fluorescence microscopy.

Immunostaining of the Golgi Apparatus for Light Microscopy 9L cells were cultured on coverslips in RPMI1640 medium with or without 10 µM retinoic acid for three hrs, then fixed for 10 min in 2% formaldehyde in PBS at 25° C., washed in PBS containing 10% FCS. Cells were incubated with monoclonal antibody to mannosidase II in PBS containing 10% FCS and 0.2% saponin for 1 hr, washed with PBS+10% serum. Cells were then incubated with fluorescein labeled goat anti-mouse IgG in PBS containing 10% serum and 0.2% saponin for 1 hr, washed three times with PBS/serum, then with PBS alone. The coverslips were mounted in 75% glycerol.

Electron Microscopy

Cells were grown in 4-well chamber slides overnight in DMEM complete medium, then cells were incubated in leucine-free RPMI1640 medium containing 10 µM retinoic acid or an equivalent amount of DMSO in control culture. After 3 hrs, cells were washed twice and fixed with 2.5% glutaraldehyde in 0.1 M Na-cacodylate buffer, pH7.2 for 60 min at room temperature, cells then were further processed for electron microscopy.

Figure 1B:
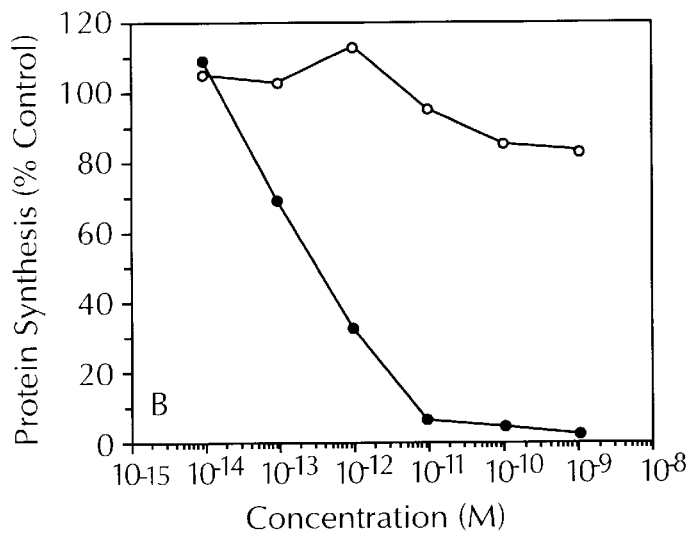
Figure 1C:
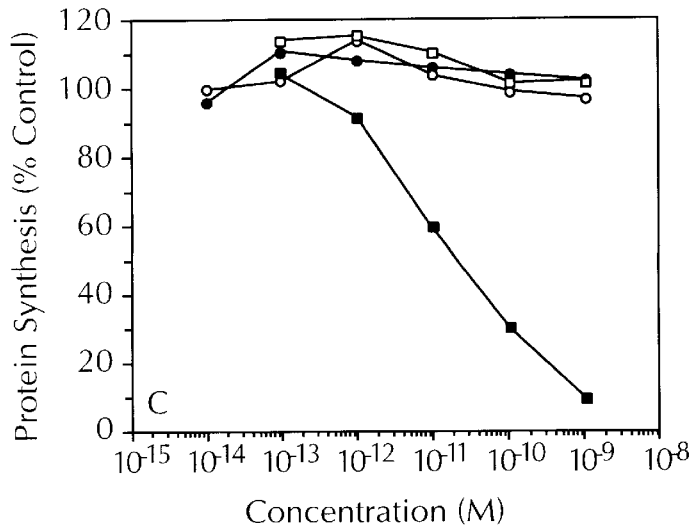

All-trans Retinoic Acid Potentiates Receptor Medicated Cytotoxicity of Immunotoxins 454A12-rRA, an immunotoxin made by a disulfide linkage between a monoclonal antibody against the human transferrin receptor (454A12) and recombinant ricin A chain (rRA), was incubated with the human glioma cell line, U251. After 3 hrs, there was no inhibition of protein synthesis up to $10^{-9}$ M 454A12-rRA. In the presence of 10 µM retinoic acid, cell protein synthesis was inhibited 50% at $10^{-13}$ M, a concentration more than 10,000 times lower than that which inhibited protein synthesis in the absence of retinoic acid (FIG. 1A). At $10^{-11}$ M immunotoxin, protein synthesis was only 20% of control after only 3 hrs. Human erythroleukemia cells, K562, were also more than 10,000 times more sensitive to 454A12-rRA in the presence of retinoic acid than in the absence of retinoic acid (FIG. 1B). However, recombinant ricin A chain by itself was not detectably potentiated by retinoic acid (FIG. 1A). 454A12-rRA was not detectably toxic to a non-target rat cell line (9L glioma) even in the presence of 10 µM retinoic acid (FIG. 1C). However, transferrin-rRA, which can bind rat 9L cells, was potentiated at least 1000 fold by 10 µM retinoic acid (FIG. 1C).

Figure 2A:
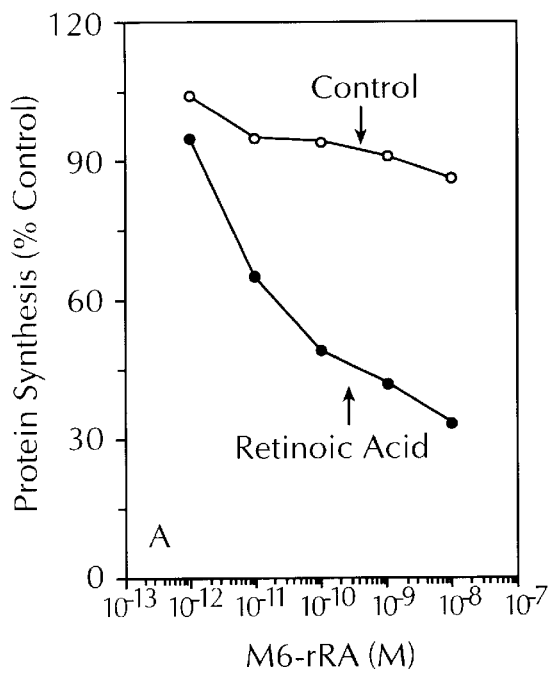
FIGS. 2A–2B shows the potentiation of 260F9-rRA and M6-rRA cytotoxicity by all-trans retinoic acid in MCF-7 and $L_2C$ cells. MCF-7 cells (FIG. 2A) or $L_2C$ cells (FIG. 2B) growing in 96-well plates were incubated with increasing concentrations of 260F9-rRA with or without 10 μM retinoic acid as indicated. After 3 hrs., the medium was removed and the cells were pulsed with $^{14}$C-leucine for another 1 hr. Cells were harvested and counted as described in Example 1.
Figure 2B:
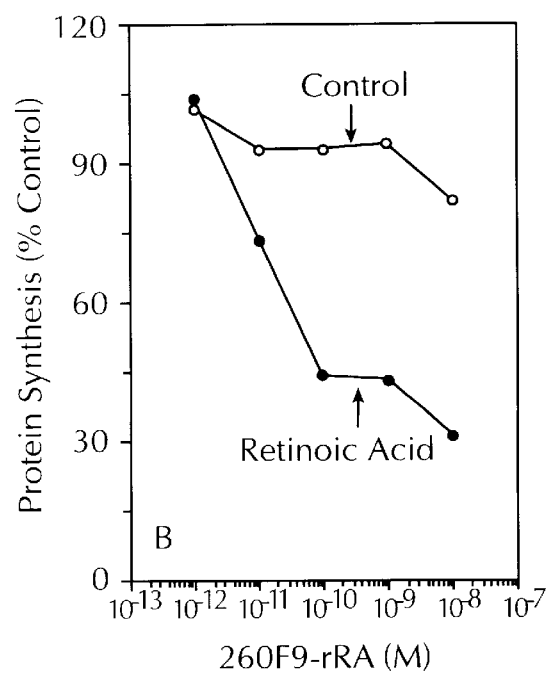

Two other immunotoxins, 260F9-rRA, against a human breast cancer antigen (Frankel, A., et al. (1985) *J. Biol. Response Modif.* 4:273–286) and M6-rRA against a B cell surface idiotype antigen (Gregg, E. N., et al. (1987) *J. Immunol.* 138:4502–4508), were also examined for potentiation of toxicity by retinoic acid. Assayed against their respective target cell lines, MCF-7 and $L_2C$, both immunotoxins were potentiated at least several orders of magnitude by 10 µM retinoic acid (FIGS. 2A and 2B).

Thus of three cell surface receptors examined, all deliver ricin A chain to the cytosol much more efficiently in the presence of retinoic acid than in the absence of retinoic acid. In contrast to the dramatic effect on receptor mediated toxicity of ricin immunotoxins by retinoic acid, no effect on fluid phase cytotoxicity of ricin A chain or immunotoxin was seen in the presence of retinoic acid.

Comparison of the Effect of All-trans Retinoic Acid, Other Retinoids, Vitamin $D_3$ and Truiodothyronine ($T_3$) On Immunotoxin Potency All-trans retinoic acid binds the RAR receptor causing it to heterodimerize with the RXR receptor and activate gene transcription (Chambon, P., et al. (1991) "The family of retinoic acid nucleic receptors" In *Retinoids*: 10 *Years On*: 10–27 J. H. Saurat (ed) (Karger/Basel); Kliewer, S. A., et al. (1992) *Nature*. 355:446–449; Zhang, X. K., et al. (1992) *Nature*. 355:441–446). 9 cis retinoic acid interacts with the RXR receptor and also stimulates dimer formation and transcription activation (Allenby, G., et al. (1993) *Proc. Natl. Acad. Sci. USA*. 90:30–34; Heyman, R. A., et al. (1992) *Cell* 68:397–406; Levin, A. A., et al. (1992) *Nature*. 355:359–361). All other cis retinoic acids do not bind either RAR or RXR. Whether or not 13-cis retinoic acid, which binds to neither RAR nor RXR (Allenby, G., et al. (1993) *Proc. Natl. Acad. Sci. USA*. 90:30–34), would affect immunotoxin activity was examined. The results indicate that 10 $\mu$M 13-cis retinoic acid potentiates immunotoxins similarly to all-trans retinoic acid (data not shown). Among other retinoids tested, 10 $\mu$M all-trans retinol shows potentiation similar to that of all-trans retinoic acid, whereas 13-cis retinal, all trans-retinal, 13-cis retinal, and 9-cis retinal do not seem to increase 454A12 MAb-rRA immunotoxin potency at 10 $\mu$M concentrations (data not shown). All-trans retinol has been recently demonstrated to be a ligand of RAR, whereas all-trans retinal does not bind to RAR (Repa, J. J., et al. (1993) *Proc. Natl. Acad. Sci. USA*. 90:7293–7297). Whether the cis-forms of retinol or retinal bind RAR or RXR receptor is not known. Thus there is some specificity among different retinoids in potentiating the cytotoxicity of immunotoxins, however retinoid receptor binding and the potentiation of the immunotoxin do not correlate. The thyroid hormone ($T_3$) receptor and the vitamin $D^3$ receptor are homologous with RAR and also form heterodimers with RXR to induce transcription activation (Kliewer, S. A., et al. (1992) *Nature* 355:446–449; Zhang, X. K., et al. (1992) *Nature* 355:441–446). Up to 1 $\mu$M thyroid hormone ($T_3$) or 1 $\mu$M 1,25-dihydroxy vitamin $D_3$ had no affect on the sensitivity of U251 to 454A12-rRA immunotoxin (data not shown).

Figure 3A:
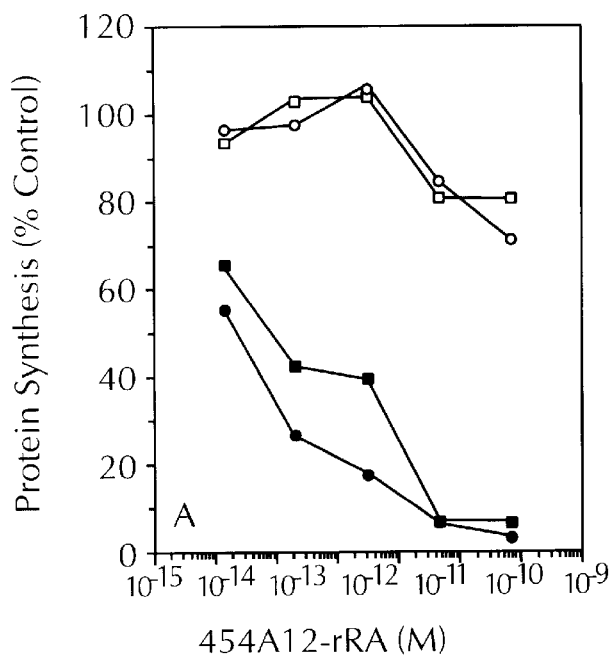
FIGS. 3A–3B shows the effect of cycloheximide and actinomycin D on all-trans retinoic acid potentiated cytotoxicity of 454A12-rRA to U251 cells. Cells were preincubated for 30 minutes (min.) with (squares) or without (circles) 1.2 ug/ml cycloheximide (FIG. 3A), or 3 hr. with (squares) or without (circles) 5.0 ug/ml actinomycin D (FIG. 3B), then further incubated with increasing concentrations of 454A12-rRA in the presence (●,■) or absence (○,□) of 10 μM retinoic acid. After 3 hrs., the medium was removed and the cells were washed with fresh medium 3 times before pulsing with $^{14}$C-leucine. Protein synthesis was measured as described in FIG. 1A–1C.
Figure 3B:
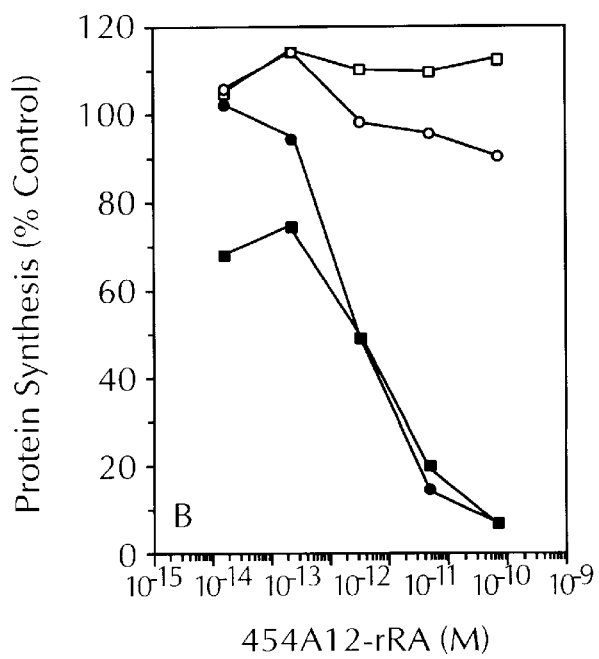

All-trans Retinoic Acid Potentiation of Immunotoxins is Independent of Gene Expression To test whether or not new gene products induced by retinoic acid result in immunotoxin sensitization, cells were incubated with cycloheximide (FIG. 3A) or actinomycin D (FIG. 3B) to prevent RNA and protein induction by retinoic acid and then exposed to retinoic acid and 454A12-rRA. FIGS. 3A and 3B shows that neither actinomycin D nor cycloheximide prevented the potentiation of 454A12-rRA cytotoxicity by retinoic acid. Thus the well established transcription activation activity of retinoic acid does not appear to be the mechanism by which retinoic acid increases cell sensitivity to immunotoxins. This conclusion is also consistent with the rapid time course of the activation by retinoic acid. After only 3 hrs, the immunotoxin is 10,000 times more toxic to cells whereas many of the effects of retinoic acid on cellular differentiation occur days after exposure to retinoic acid. Apparently retinoic acid has a direct effect on cells that causes the increased sensitivity to immunotoxins.

All-trans Retinoic Acid Potentiates Immunotoxins at Steps Subsequent to Cell Surface Receptor Binding Immunotoxins may be Potentiated by Increasing the amount of immunotoxin bound to cell surface receptors or by increasing the delivery of surface bound immunotoxin to the cytosol compartment. To examine if retinoic acid increases the binding of immunotoxins to target cells, cells were incubated with 454A12-rRA for 2 hrs at 4° C. then washed to remove unbound immunotoxin. The cells were divided in half and one half was incubated in the presence and one half was incubated in the absence of retinoic acid for 3 hrs at 37° C. and then the cells were pulsed with $^{14}$C-leucine and harvested. The results show that the potentiation of 454A12-rRA occurs even in cells washed prior to adding the retinoic acid (data not shown) indicating that the effect of retinoic acid is not a consequence of increased receptor binding. This leaves intracellular routing and passage into the cytosol as the likely effect retinoic acid has upon immunotoxin potency.

Figure 4:
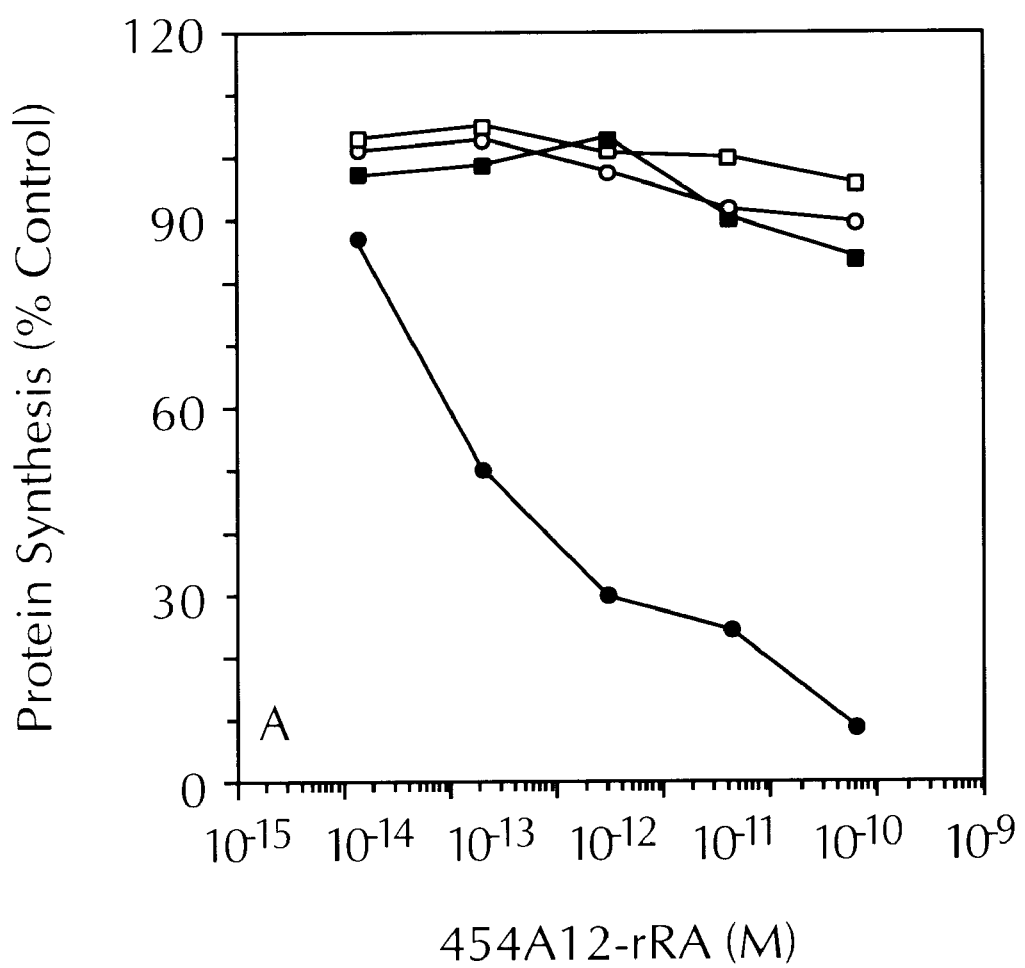
FIG. 4 shows that the Brefeldin A blocks all-trans retinoic acid potentiated cytotoxicity of 454A12-rRA immunotoxin. U251 cells were incubated with increasing concentrations of 454A12-rRA at 37° C. with (●,■) or without (○,□) of 10 μM retinoic acid in the presence (squares) or absence (circles) of 10 μg/ml brefeldin A. After 3 hrs., protein synthesis was assayed as described for FIGS. 1A–1C.
Figure 5A:
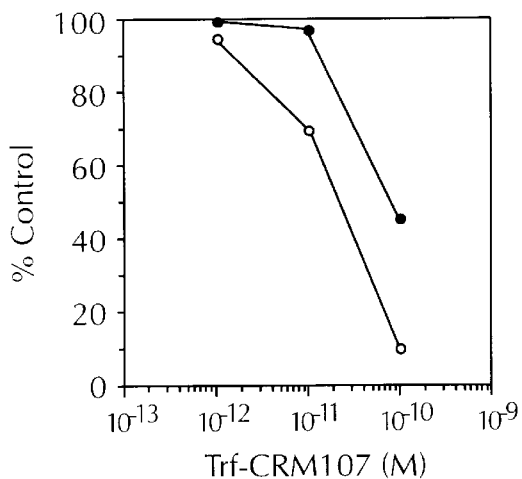
FIGS. 5A–5D show effects of all-trans retinoic acid on the cytotoxicity of diphtheria toxin (DT), Pseudomonas exotoxin (PE), tfn-CRM107, and tfn-PE in U251 cells. U251 cells were incubated with increasing concentrations of DT, PE, tfn-CRM107, and tfn-PE as indicated in the figure with (●) or without (○) 10 μM all-trans retinoic acid for 3 hrs. Protein synthesis was assayed as described for FIG. 1A–1C.
Figure 5B:
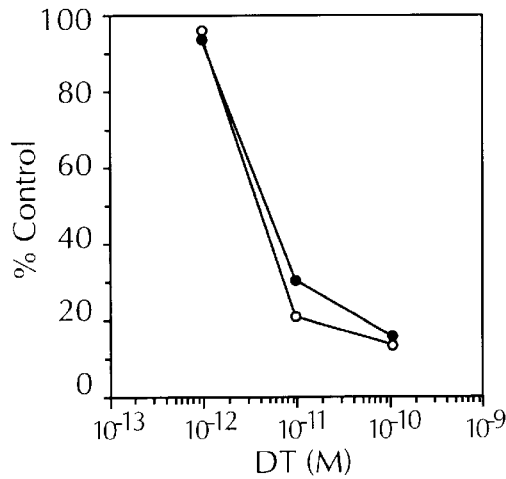
Figure 5C:
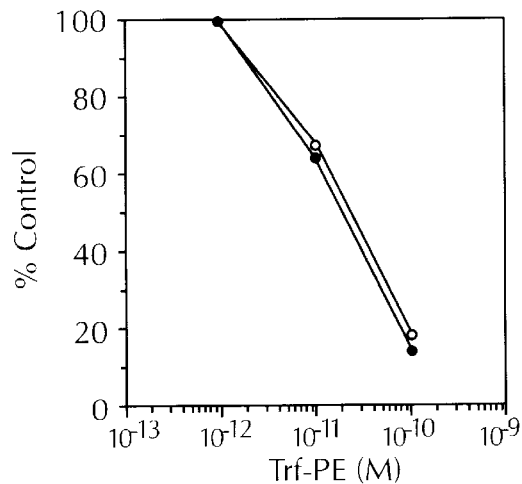
Figure 5D:
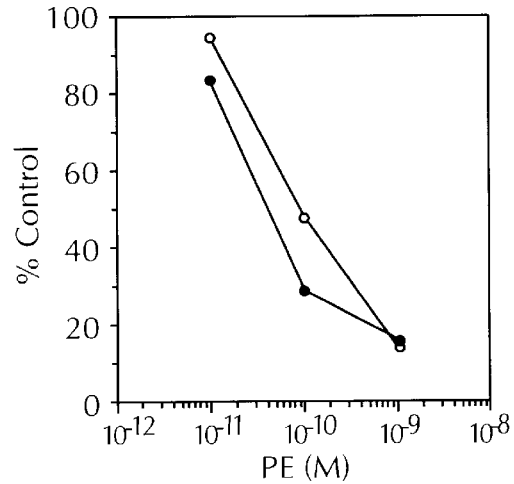

Brefeldin A blocks the All-trans Retinoic Acid Potentiation of Immunotoxin Toxicity The Golgi has been implicated in the efficient routing of native ricin to the cytosol through functions of the ricin B chain (Johnson, V. G., et al. (1991) "Intracellular Routing and membrane translocation of and ricin" In *Intracellular Trafficking of Proteins*: 183–225 Steer and Hanover (eds) (Kreger/Basal. To examine whether or not retinoic acid may affect routing of immunotoxins through the Golgi apparatus, the effect of brefeldin A (BFA) on the retinoic acid potentiation of 454A12-rRA was examined. BFA, by inhibiting vesicular transport from the endoplasmic reticulum (ER) to the Golgi, results in collapse of the cis-Golgi apparatus blocking the retrograde vesicular transport of vesicles from the Golgi to the ER (Doms, R. W., et al. (1989) *J. Cell. Biol.* 109:61–72; Lippincott-Schwartz, J., et al. (1989) *Cell.* 56:801–813). BFA was incubated with U251 cells in the presence of 454A12-rRA and retinoic acid. FIG. 4 shows that BFA completely blocks the potentiation of toxicity by retinoic acid. This indicates that 454A12-rRA routes through a BFA sensitive compartment, possibly the Golgi apparatus or the endoplasmic reticulum, in the presence of retinoic acid.

The Effect of All-trans Retinoic Acid on the Potency of Other Protein Toxins and Immunotoxins In contrast to ricin A chain immunotoxins, that are potentiated by ionophores that disrupt the Golgi apparatus, diphtheria toxin (DT) and Pseudomonas exotoxin A (PE) and their respective immunotoxins, are blocked by monensin, a carboxylic ionophore. The effect of retinoic acid on the toxicity of PE, DT and transferrin coupled to PE and transferrin coupled to a diphtheria toxin mutant, CRM107 was examined. FIG. 5 shows that, in contrast to 454A12-rRA, DT, PE and transferrin-CRM107 (tfn-CRM107) and transferrin-PE (tfn-PE) are not potentiated by retinoic acid. DT and tfn-CRM107 are actually inhibited a small extent by retinoic acid. These results are consistent with the model that retinoic acid alters the routing of immunotoxins through the Golgi apparatus with some degree of selectivity. The effect of retinoic acid differs markedly from that of monensin, however. Retinoic acid has little effect on DT and PE whereas monensin blocks DT over 1000 times.

Figure 6A:
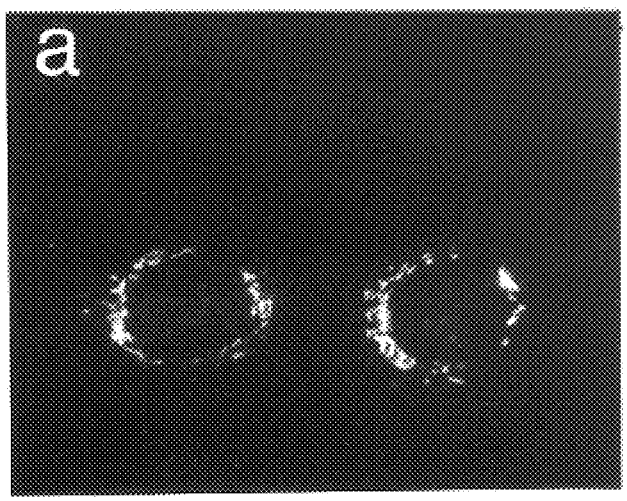
FIGS. 6A–6C shows all-trans retinoic acid treatment causes different distribution of Golgi apparatus stained with monoclonal antibody (MAb) against mannosidase II. 9L cells grown on cover slips in leucine-free RPMI.1640 medium were treated with (FIGS. 6B, 6C) or without (FIG. 6A) 10 μM retinoic acid. After 2 hrs., the medium was removed and the cells were washed twice. Cells were then either fixed in 2% formaldehyde (FIGS. 6A and 6B) or incubated further in DMEM complete medium for 60 min (FIG. 6C), then fixed in 2% formaldehyde. Cells were incubated with MAb against mannosidase II in PBS containing 10% FCS and 0.2% saponin for 60 min., and washed. Cells were then incubated with fluorescein-labeled goat anti-mouse IgG in phosphate buffered saline (PBS) containing 10% FCS and 0.2% saponin for another 60 min. Cells were washed and mounted in 75% glycerol.
Figure 6B:
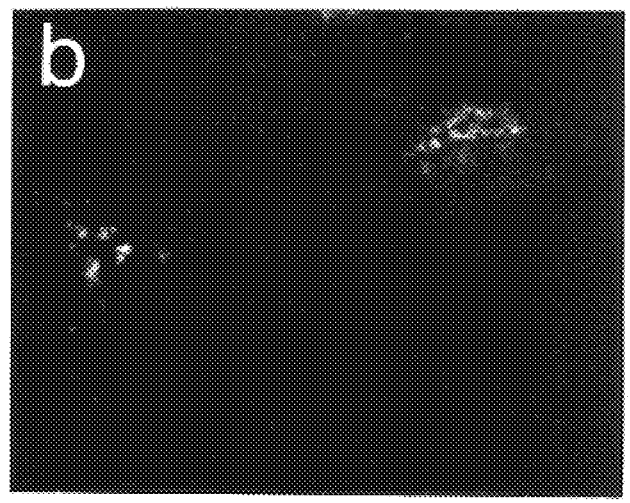
Figure 6C:
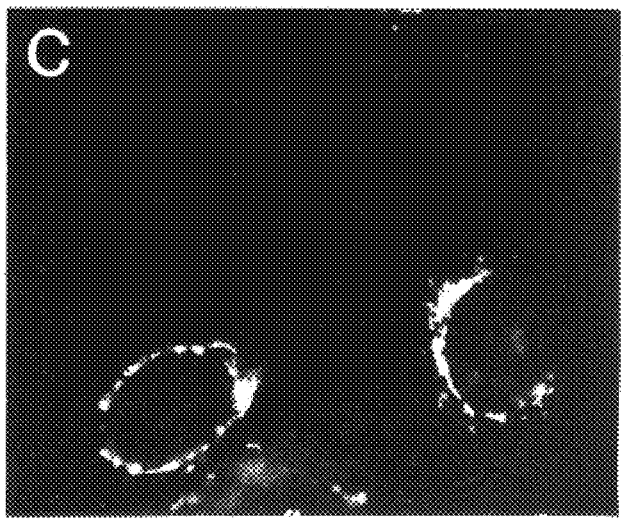

All-trans Retinoic Acid Alters the Golgi Apparatus Morphology Visualized by Immunostaining with an Anti-mannosidase II Monoclonal Antibody and by Vital Staining with $C_6$-NBD-ceramide Immunostaining of the Golgi apparatus with a monoclonal antibody against the Golgi marker, mannosidase II, shows that retinoic acid causes a marked perturbation in the Golgi apparatus (FIG. 6B). In control 9L cells the Golgi apparatus has a typical perinuclear network appearance (FIG. 6A). After treatment of 9L cells with 10 μM retinoic acid the Golgi apparatus becomes clumped and diffuse with no perinuclear distribution. Upon removal of the retinoic acid the typical perinuclear distribution of the Golgi apparatus reassembles by 60 min (FIG. 6C). Thus retinoic acid causes a reversible dissolution of the perinuclear Golgi network when observed with an anti-mannosidase II antibody.

Figure 7A:
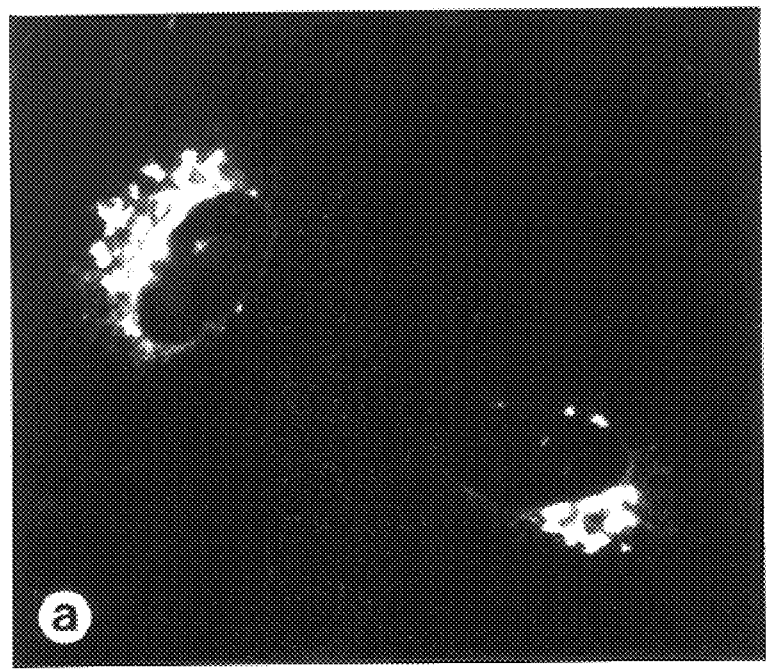
FIGS. 7A–7D shows all-trans retinoic acid treatment either protects or disrupts the specific vital staining of the Golgi apparatus with N-[7-(4-nitrobenzo-2 oxa-1,3-diazole)]-6-aminohexanoyl-d-erythro-sphingosine ($C_6$-NBD-ceramide). U251 cells grown on glass cover slips in leucine-free RPMI1640 medium were tested with (FIG. 7B) or without (FIG. 7A) 10 μM retinoic acid. After 2 hrs. the medium was removed and the cells were washed twice. Cells were then incubated in the same medium with 5 μM fluorescently labeled $C_6$-NBD-ceramide in the absence of all-trans retinoic acid at 2° C. for 1 h. washed twice and incubated for 30 min. at 37° C. Cells were carefully mounted on glass slides and photographed under a fluorescent microscope.
Figure 7B:
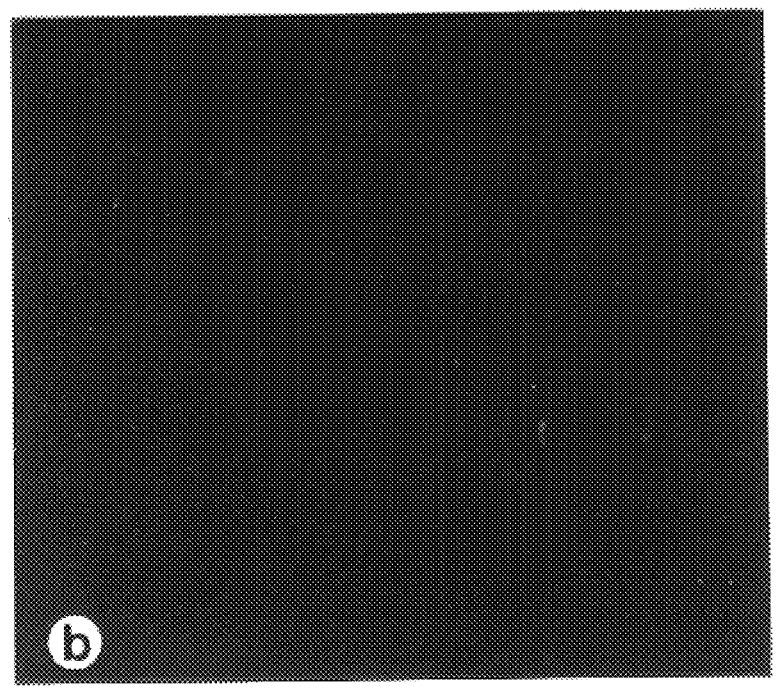
Figure 7C:
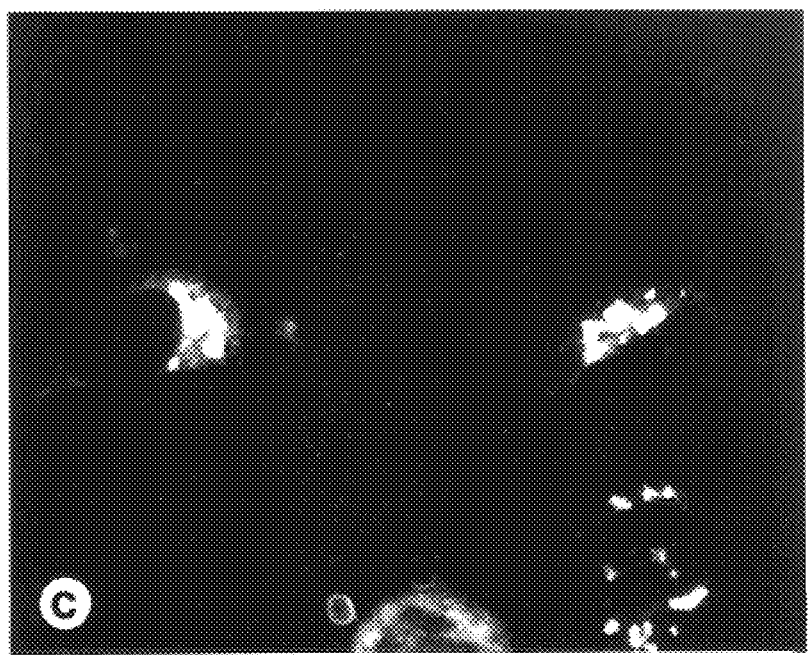
Figure 7D:
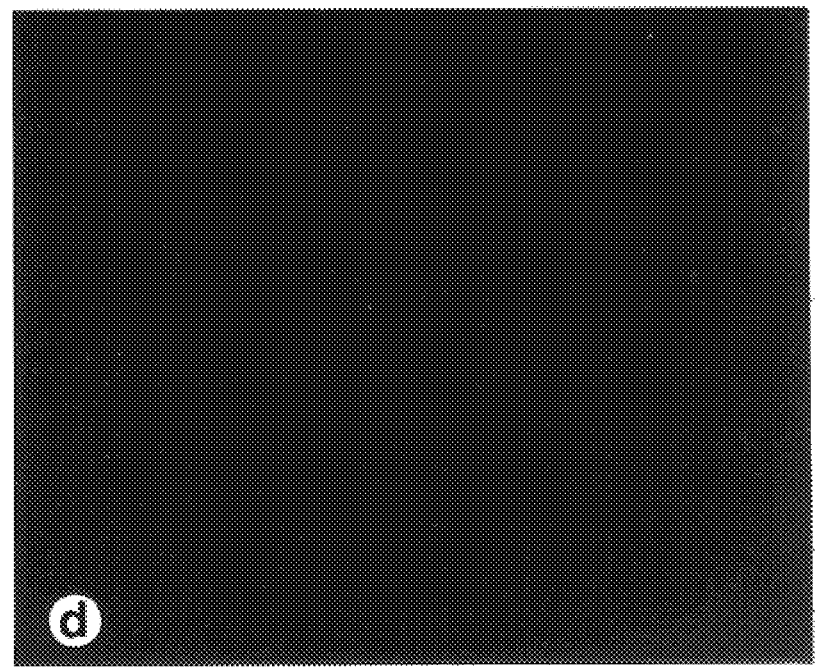

$C_6$-NBD-ceramide, a fluorescent dye, is another powerful tool to study the structure and function of the Golgi apparatus in living cells (Lipsky, N. G., et al. (1985) *Science* 228:745–747). $C_6$-NBD-ceramide staining of the Golgi apparatus in U251 cells in the presence and absence of retinoic acid (FIGS. 7A–7D) was examined. The Golgi apparatus in control cells (FIG. 7A) shows a perinuclear appearance as previously reported (Lipsky, N. G., et al. (1985) *Science* 228:745–747). In cells treated with 10 μM retinoic acid for 2 hrs there is a dramatic inhibition of Golgi fluorescence (FIG. 7B). If the Golgi apparatus is stained first with $C_6$-NBD-ceramide and then incubated with retinoic acid (FIG. 7D) or without (FIG. 7C) for 2 hrs, cells show a dramatic decrease in fluorescence labeling. Thus retinoic acid disrupts the normal Golgi apparatus when examined with the vital dye, $C_6$-NBD-ceramide.

Figure 8A:
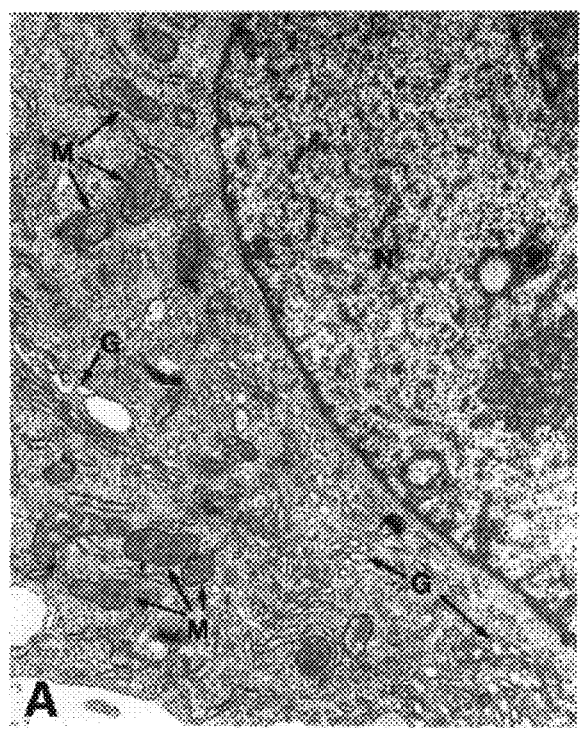
FIGS. 8A–8D shows all-trans retinoic acid treatment causes disappearance of the Golgi apparatus and appearance of perinuclear vacuolization. Human U251 cells grown in 4-well chamber slides were incubated in leucine-free RPMI1640 medium with or without 10 μM retinoic acid, after 3 hr., cells were washed twice and fixed with 2.5% glutaraldehyde in 0.1 M Na-cacodylate buffer, pH 7.2 for 60 min. at room temperature, cells then were further processed for electron microscopy (M, mitochondrium; G, Golgi apparatus; N, nucleus; thick arrow, vacuolized structures).
Figure 8B:
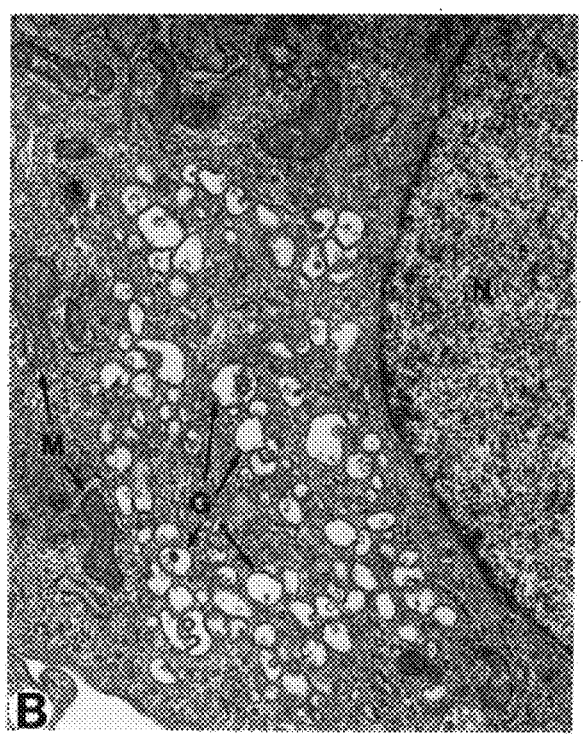
Figure 8C:
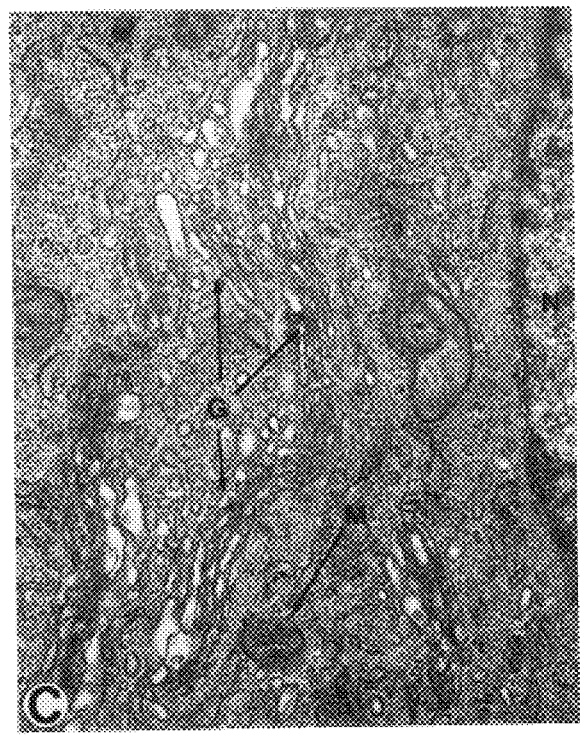
Figure 8D:
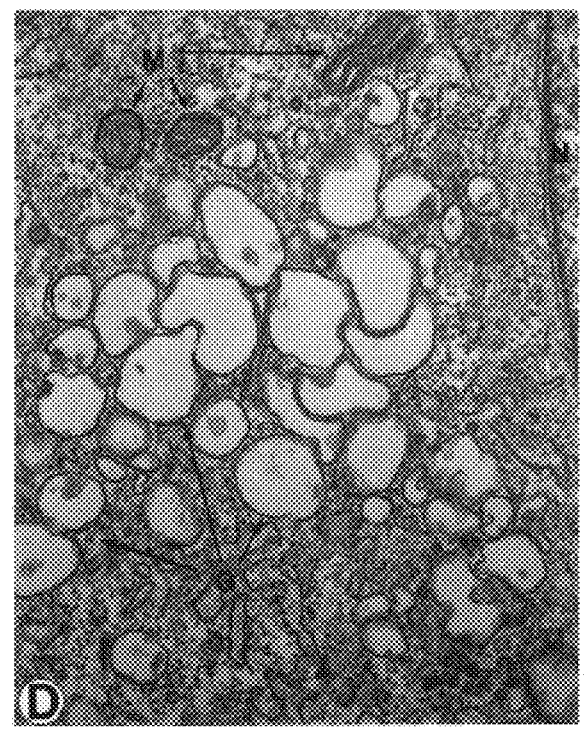
Figure 9A:
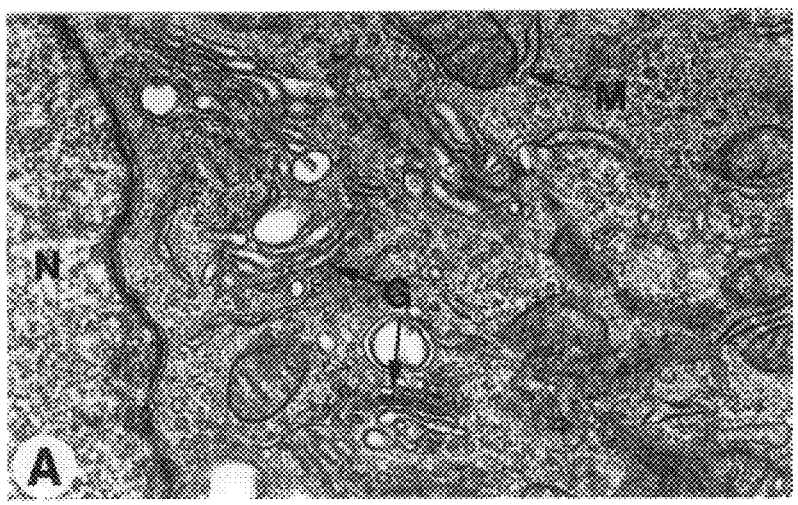
FIGS. 9A–9C shows all-trans retinoic acid caused vacuolization disappears after removing the drug. Rat 9L cells cultured in 4-well chamber slides were incubated with (FIGS. 9B, 9C) or without (FIG. 9A) 10 μM retinoic acid. After 3 hrs. cells were washed twice and either fixed (FIGS. 9A and 9B) with glutaraldehyde as described for FIGS. 8A–8D or further: incubated in complete DMEM medium for 60 min.
Figure 9B:
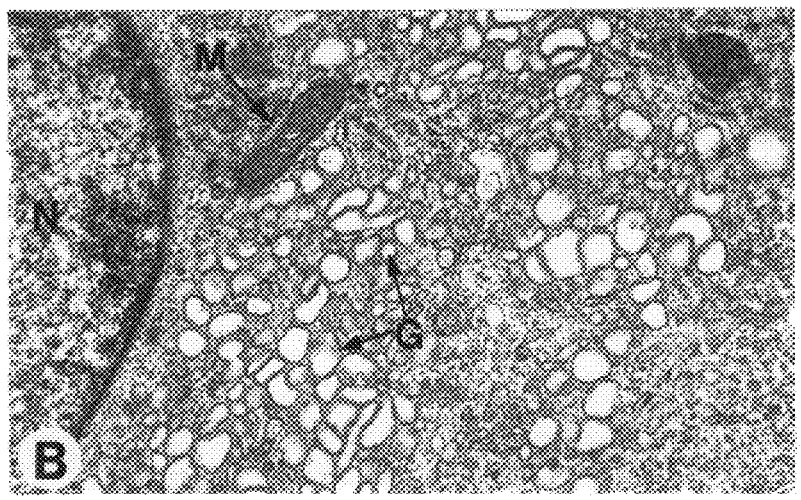
Figure 9C:
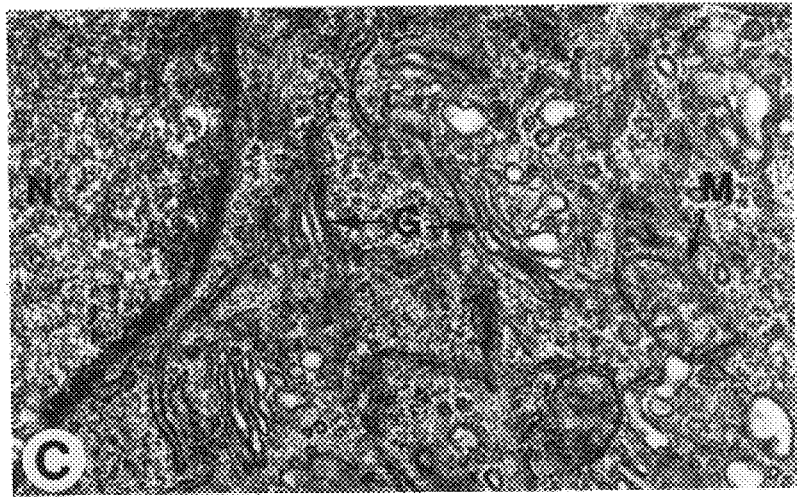

All-trans Retinoic Acid Treatment Causes a Reversible Disappearance of the Golgi Apparatus Observed by Electron Microscopy To further examine the status of the Golgi apparatus in retinoic acid treated cells utilizing electron microscopy. Retinoic acid treatment of U251 cells correlated with a complete disappearance of normal Golgi cisterna and the appearance of large perinuclear vacuoles (FIGS. 8B and 8D). Retinoic acid caused a similar disappearance of the Golgi apparatus and vacuolization in 9L cells (FIG. 8B). Upon removal of the retinoic acid, normal Golgi stacking reappeared and the swollen vacuoles disappeared within 60 min. (FIG. 9C). These results indicate that the vacuolized structures may at least partially be composed of dilated Golgi apparatus. Monensin causes massive dilation of the Golgi apparatus (Ledger, et al *J. Cell. Biol.*, 87:663–671, 1980) to the appearance of retinoic acid treated cells and also causes potentiation of ricin A chain immunotoxins. The effect of retinoic acid on the Golgi may relate to the mechanism of immunotoxin potentiation.

All-trans retinoic acid selectively increases the potency of certain immunotoxins. Ricin A chain containing immunotoxins, via three different receptors, on several different cell lines, are potentiated by retinoic acid whereas immunotoxins with diphtheria toxin and Pseudomonas exotoxin are not. Thus the effect seems to be independent of the cell surface receptor yet specific to the toxin. Only receptor mediated pathways of intoxication appear to be affected by retinoic acid. Ricin A chain alone, and non-binding immunotoxins are not detectably potentiated by retinoic acid.

The sensitization of cells to immunotoxins by retinoic acid is completely blocked by brefeldin A. Brefeldin A blocks the vesicular transport from the ER to the cis-Golgi apparatus causing a collapse of the cis-Golgi and a termination of the retrograde vesicular transport from the cis-Golgi back to the ER (Lippincott-Schwartz, J.,.et al. (1989) *Cell.* 56:801–813). The block of the retinoic acid potentiation by brefeldin A suggests that retinoic acid stimulates transport of the immunotoxins through the cis-Golgi, possibly to the ER en route to the cytosol. Brefeldin A has also been shown to affect endosomes, lysosomes, and the trans-Golgi network (Lippincott-Schwartz, J., et al. (1991) *Cell* 67:601–616, Pelham, H. R. B. (1991) *Cell*. 67:449–451).

Retinoic acid seems to be having an effect on cells vis a vis their toxin sensitivity much like that of lysosomotropic agents such as monensin. As monensin disrupts intracellular traffic and causes morphologic alterations in the Golgi apparatus (Ledger, et al *J. Cell Biol*., 87:663–671, 1980) retinoic acid treated cells were examined by immunostaining with an anti-mannosidase II MAb, with the vital Golgi stain, $C_6$-NBD ceramide, and by EM. Examination of the Golgi apparatus with a lipid that specifically stains the Golgi in living cells (Lipsky, N. G., et al. (1985) *Science* 228:745–747), fluorescent $C_6$-NBD-ceramide, shows that retinoic acid treatment caused a dramatic disappearance of the Golgi apparatus staining. This is not because of decreased $C_6$-NBD-ceramide uptake since treatment with retinoic acid following $C_6$-NBD-ceramide staining also causes a dramatic decrease in fluorescence intensity of the Golgi apparatus. Immunostaining of mannosidase II demonstrated the disruption of the perinuclearly located Golgi apparatus by retinoic acid treatment, and this disruption was readily reversible upon removal of the retinoic acid. Electron microscopy also shows a complete disappearance of the Golgi stacking, and the appearance of a perinuclear vacuolization upon exposure of cells to retinoic acid. This vacuolization is reversed and normal Golgi apparatus reappears after removal of retinoic acid indicating the vacuolized structures are derived at least partially from the swollen Golgi apparatus. The vacuolization seen by EM caused by retinoic acid in two different cell lines (U251, 9L) resembles that caused by monensin (Ledger, et al *J. Cell Biol*., 87:663–671, 1980). However, the results of $C_6$-NBD-ceramide staining of retinoic acid treated cells are opposite to those seen in monensin treated cells. With monensin, $C_6$-NBD-ceramide staining of the Golgi is more intense and punctate (Lipsky, N. G., et al. (1985) *J. Cell Biol*. 100:27–34) whereas retinoic acid eliminates $C_6$-NBD-ceramide staining. Brefeldin A causes diminution of the Golgi apparatus by EM and with NBD-ceramide in appropriate cell types (Chen, C. H., et al. (1992) *Exp. Cell Res*. 203:321–328; Ktistakis, N. T., et al. (1991) *J. Cell Biol* 113:1009–1023). Thus, the effects of retinoic acid on the Golgi presents a new pattern relative to that seen with previously described drugs.

The effects of retinoic acid on ricin, diphtheria toxin, and Pseudomonas exotoxin are consistent with this model that retinoic acid alters the endocytotic routing in cells. Native ricin, modeccin and abrin toxicity are blocked a small amount by 10 $\mu$M retinoic acid in HeLa cells and Vero cells (Sandvig, K., et al. (1981) *Biochem. J*. 194:821–827). Retinoic acid also protects U251 cells from ricin toxicity (data not shown). These results and the potentiation of ricin A chain immunotoxins by retinoic acid are similar to the effects seen with lysosomotropic amides and ionophores. Native ricin contains a B chain that is thought to use a galactose binding function, intracellularly, to route the toxin through the Golgi apparatus to reach the cytosol (Johnson, V. G., et al. (1991) "Intracellular Routing and membrane translocation of diphtheria toxin and ricin" In Intracellular Trafficking of Proteins: 183–225 Steer and Hanover (eds) (Karger/Basel). The galactose binding activity may allow ricin, in the trans-Golgi, to bind to KDEL receptor-like glycoproteins that cycle to and from the cis-Golgi and the endoplasmic reticulum (ER) (Zhang, X. K., et al. (1992) Nature 355:441–446). Immunotoxins that lack a B chain are much less potent, apparently due to a deficiency in intracellular routing. Ricin A chain immunotoxins may recycle through the trans-Golgi back to the cell surface repeatedly in the absence of a B chain and disruption of the Golgi with monensin or retinoic acid may allow trans-Golgi to cis-Golgi movement, sensitizing the cell to the toxin. Retinoic acid, by disrupting the Golgi, may slightly disrupt the efficient B chain mechanism of Golgi transport resulting in a small inhibition of native ricin toxicity while potentiating the inefficient ricin A chain immunotoxin routing.

Diphtheria toxin requires a low intravesicular pH for the toxin B chain to mediate membrane transport to the cytosol (Draper, R., et al. (1980) *J. Cell Biol.* 87:849–854). Endosomes or lysosomes may be the optimal intracellular site for DT entry into the cytosol and, as brefeldin A does not inhibit DT, there is no evidence that routing to or through the Golgi is needed for DT toxicity. Monensin and lysosomotropic amines block DT presumably simply by neutralizing low pH in endosomes and lysosomes. Retinoic acid does not inhibit the intracellular routing of DT to these compartments nor does it appear to alter the intracellular pH of these compartments from which DT enters the cytosol.

PE, like DT, is blocked by lysosomotropic agents but appears to route through different intracellular compartments on its way to the cytosol (Fitzgerald, D., et al. (1991) "Pseudomonus exotoxin and derived conjugates: interactions with mammalian cells" *In: Intracellular trafficking of proteins*. 226–247 Steer and Hanover (eds) Cambridge/England). PE contains a KDEL-like C-terminal sequence that can bind the KDEL receptor in the Golgi and is proposed to route PE out of the Golgi to the ER for efficient transport to the cytosol (Chaudhary, V.K., et al. (1990) *Proc. Natl. Acad. Sci. USA*. 87:308–312). Consistent with this model brefeldin A blocks PE toxicity (Yoshida, T., et al. (1991) *Exp. Cell Res.* 192:389–395). The inhibition of PE by monensin may result from its effect on the Golgi apparatus. Retinoic acid had little effect on PE arguing that retinoic acid is very specific in its cellular perturbation or that PE is already adept at Golgi to ER transfer and retinoic acid does not further facilitate this step. Even when different toxins enter cells via the same receptor they are affected differently by retinoic acid. Tfn-PE and tfn-CRM107, two immunotoxins that traffic into cells via the transferrin receptor are not affected by retinoic acid whereas tfn-rRA and 454A12 rRA, ricin A chain immunotoxins that utilize the transferrin receptor, are strongly potentiated.

The potentiation of immunotoxins by retinoic acid and monensin, however, shows some significant differences. Retinoic acid has little affect on DT or PE whereas monensin strongly blocks both DT and PE and BFA can block retinoic acid mediated immunotoxin potentiation but not monensin mediated immunotoxin potentiation (data not shown). Thus, similar to the results form morphology studies by EM, immunostaining and $C_6$-NBB-ceramide staining, retinoic acid shows some characteristics of immunotoxin potentiation similar to monensin and some very different from monensin.

The effect of retinoic acid on immunotoxin activity is not blocked by cycloheximide or actinomycin D indicating that the retinoic acid directly affects cells and does not function via induction of new gene expression. Furthermore, examining a series of agents that bind or heterodimerize members of the retinoic acid receptor, e.g., all-trans retinoic acid, all-trans retinol, thyroxine ($T_3$) and vitamin $D_3$, and retinoids that do not bind the receptors, e.g. all-trans retinal, 13-cis retinoic acid, and other cis-forms of retinol and retinal, shows a lack of correlation between immunotoxin activation and RAR or RXR receptor interaction. Thus the well established transcription activation activity of retinoic acid does not appear to be the mechanism by which retinoic acid increases cell sensitivity to immunotoxins. The morphological effects of retinoic acid on the Golgi apparatus as shown by vital staining and by EM study likely relate to the mechanism of immunotoxin potentiation. The molecular mechanisms of this new activity of certain retinoids remains to be discovered.

EXAMPLE 2

Treatment of Human Breast Carcinoma

In patients having breast carcinoma, the immunotoxin monoclonal antibody 260F9-ricin A chain is injected intravenously (I.V.) at a concentration of about 0.01 mg/Kg as a one hour infusion. The trans retinoic acid is administered orally at a concentration of about 2000 mg/Kg body weight. The immunotoxin and trans retinoic acid are administered daily for 6–8 days. Clinical parameters of the patients are monitored.

EXAMPLE 3

Treatment of Human Brain Tumors

In one group of patients, the immunotoxin transferrin-ricin A chain is directly infused into human brain tumors at 0.5 $\mu$g/ml, 20 $\mu$g total dose, as disclosed in Bobo, R. H. et al *Proc. Nat'l Acad Sci USA* 91:2076–2080, 1994, with trans retinoic acid given orally at 2000 mg/kg.

In a second group of patients, the immunotoxin transferrin-ricin A chain is directly infused into human brain tumors at 0.5 $\mu$g/ml, 20 $\mu$g total dose, with trans retinoic acid mixed with the immunotoxin at a 1 mM concentration and infused with the immunotoxin.

In a third group of patients, the immunotoxin, monoclonal antibody 260F9-ricin A chain is injected i.v. at 0.4 mg/kg daily for 5 days, with trans retinoic acid given orally at 2000 mg/kg.

Clinical parameters of the patients are monitored including tumor size, change in MRI brain scan, and survival.

EXAMPLE 4

Method of Treatment of Bone Marrow Cells For Transplantation

Bone marrow is aspirated from the iliac crest of the donor. Multiple aspirations of 5 ml each, yielding a total of 10 ml/kg of the recipients body weight (600–1200 ml) are obtained. The marrow is drawn through heparinized needles and placed into heparinized, buffered culture medium. The mixture is gently filtered through a fine stainless steel mesh screen to produce a single-cell suspension. If the donor and recipient are not ABO-compatible, the erythrocytes are removed from the donor's marrow using specific blood group antibody and complement or equivalent procedure.

For treatment of allogeneic bone marrow to inhibit or prevent graft-vs-host disease, one liter of the allogenic cells are treated with $10^{-9}$ M of anti-donor T cell antibody-ricin A chain immunotoxin and 10 $\mu$M retinoic. The bone marrow cells are incubated at 37° C. for approximately 4 hours. After treatment, about $2\times10^8$ to $6\times10^8$ nucleated marrow cells/kg of the recipient's body weight are infused into the recipient together with a 20–30% volume of erythrocytes.

For treatment of autologous bone marrow to inhibit tumor cells, the autologous cells are treated with $10^{-9}$M of anti-tumor cell antibody-ricin A chain immunotoxin and 10 $\mu$M retinoid. The cells are incubated and reinfused as described above. The autologous donor is treated with chemotherapy and/or irradiation prior to reinfusion.

For treatment of autologous bone marrow to inhibit the growth of HIV-infected cells, the autologous cells are treated with $10^{-9}$M of CD4-ricin A chain and 10 $\mu$M retinoid. The cells are incubated with the composition as described above and reinfused.

Although the present invention has been described on some detail by way of illustration and examples for purposes of clarity and understanding it will be obvious that certain changes and modifications may be practiced within the scope of the appended claims.

What is claimed is:

1. An in vitro method to screen for a retinoid that is capable of potentiating the activity of an immunotoxin comprising:
   (a) exposing mammalian target cells to an immunotoxin and a retinoid to be screened for potentiating activity;
   (b) assessing growth inhibition of the target cells relative to control cells that are exposed to said immunotoxin alone; and
   (c) correlating the growth inhibition of the target cells relative to the control cells with the potentiating ability of said retinoid on said immunotoxin.

2. The method of claim 1 wherein the immunotoxin and retinoid are added to the target cells simultaneously.

3. The method of claim 1 wherein the immunotoxin and retinoid are sequentially added to the target cells.

4. The method of claim 1, wherein said retinoid is selected from the group consisting of all-trans retinoic acid, 13-cis retinoic acid, and all-trans retinol.

5. The method of claim 1, wherein a toxin comprising said immunotoxin is selected from the group consisting of ricin A, abrin A chain, saporin, gelonin, plant ribosome inactivating protein, trichosanthin, modeccin, ribonucleases, and angiogenin.

6. The method of claim 1, wherein said mammalian target cells are selected from the group consisting of cancer cells, HIV-infected cells, *Mycobacterium tuberculosis*-infected cells, Measles virus-infected cells, Hepatitis-infected cells, and *Legionella pneumophilia*-infected cells.

7. The method of claim 1, wherein said growth inhibition is determined by a decrease in protein synthesis of said mammalian target cells relative to said control cells.

8. The method of claim 1, wherein said growth inhibition is determined by an increase of cytotoxicity of said mammalian target cells relative to said control cells.

* * * * *